US011116469B2

(12) United States Patent
Bartl et al.

(10) Patent No.: US 11,116,469 B2
(45) Date of Patent: Sep. 14, 2021

(54) METHOD FOR DETERMINING A RELATIVE POSITION OF AN OBJECT IN RELATION TO AN X-RAY IMAGING APPARATUS

(71) Applicant: Siemens Healthcare GmbH, Erlangen (DE)

(72) Inventors: Peter Bartl, Puschendorf (DE); Robert Brauweiler, Baiersdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/782,244

(22) Filed: Feb. 5, 2020

(65) Prior Publication Data

US 2020/0268328 A1    Aug. 27, 2020

(30) Foreign Application Priority Data

Feb. 21, 2019  (DE) .......................... 102019202359.2

(51) Int. Cl.
*A61B 6/02*       (2006.01)
*A61B 6/04*       (2006.01)
(Continued)

(52) U.S. Cl.
CPC .............. *A61B 6/545* (2013.01); *A61B 6/022* (2013.01); *A61B 6/0492* (2013.01); *A61B 6/06* (2013.01);
(Continued)

(58) Field of Classification Search
CPC ........... A61B 6/12; A61B 6/0492; A61B 6/06; A61B 6/4441; A61B 6/5235; A61B 6/542; A61B 6/589
(Continued)

(56) References Cited

U.S. PATENT DOCUMENTS 5,299,254 A  *  3/1994  Dancer ................... A61B 6/12
                                                        378/162
5,684,855 A     11/1997  Aradate
(Continued)

FOREIGN PATENT DOCUMENTS

DE       102008044437 A1    12/2009
DE       102010040963 A1    3/2012
(Continued)

OTHER PUBLICATIONS

German Office Action for German Application No. 10 2019 202 359.2 dated Dec. 23, 2019.

*Primary Examiner* — Thomas R Artman
(74) *Attorney, Agent, or Firm* — Lempia Summerfield Katz LLC

(57) ABSTRACT

A method is provided for determining a relative position of an object in relation to an x-ray imaging apparatus for creating an x-ray and a recorded image. The method includes bringing an object in a ray path of an x-ray into a first position. In a first recorded image, at least one defined geometry in and/or on the object is imaged. A measure for a change in the first focus point towards a second focus point is undertaken at the x-ray source. In the second recorded image, the at least one defined geometry is imaged. A distance from the object to the x-ray source and/or to the x-ray detector is determined based on the change in the focus point, as well as on the basis of the images of the at least one defined geometry in the first and the second recorded image.

20 Claims, 4 Drawing Sheets

(51) Int. Cl.
*A61B 6/06* (2006.01)
*A61B 6/12* (2006.01)
*A61B 6/00* (2006.01)

(52) U.S. Cl.
CPC .......... *A61B 6/4021* (2013.01); *A61B 6/4028* (2013.01); *A61B 6/4441* (2013.01); *A61B 6/5235* (2013.01); *A61B 6/542* (2013.01); *A61B 6/589* (2013.01); *A61B 6/12* (2013.01); *A61B 6/4452* (2013.01); *A61B 6/588* (2013.01)

(58) Field of Classification Search
USPC .......................................................... 378/62
See application file for complete search history.

(56) References Cited

U.S. PATENT DOCUMENTS

| | | | | |
|---|---|---|---|---|
| 6,222,904 B1* | 4/2001 | Berestov | ................ | A61B 6/022 378/154 |
| 9,427,198 B2* | 8/2016 | Steinhauser | .............. | A61B 6/46 |
| 2002/0065461 A1* | 5/2002 | Cosman | ................ | A61B 90/16 600/426 |
| 2005/0078788 A1* | 4/2005 | Cohen | .................... | G01S 5/166 378/62 |
| 2005/0201515 A1* | 9/2005 | Mitschke | ............. | A61B 5/1135 378/62 |
| 2007/0025507 A1* | 2/2007 | Grass | .................... | G06T 11/005 378/62 |
| 2008/0089468 A1* | 4/2008 | Heigl | ..................... | A61B 6/032 378/20 |
| 2010/0040196 A1* | 2/2010 | Zhang | ................... | A61B 6/504 378/42 |
| 2012/0039438 A1* | 2/2012 | Parham | ................ | A61B 6/5282 378/62 |
| 2012/0069950 A1 | 3/2012 | Grasruck | | |
| 2013/0129038 A1* | 5/2013 | Wang | ..................... | A61B 6/482 378/37 |
| 2015/0071405 A1* | 3/2015 | Jacobs | ................... | A61B 6/545 378/41 |
| 2015/0146843 A1* | 5/2015 | Steinhauser | .......... | A61B 6/035 378/4 |
| 2017/0000451 A1* | 1/2017 | Aspelund | ............... | A61B 6/582 |
| 2017/0354386 A1* | 12/2017 | Yu | ........................ | A61B 6/4405 |
| 2019/0282195 A1 | 9/2019 | Dressler | | |
| 2020/0268328 A1* | 8/2020 | Bartl | ...................... | A61B 6/589 |

FOREIGN PATENT DOCUMENTS

EP             3539474 A1     9/2019
WO    WO-2006006260 A1 *   1/2006  ............ A61B 6/022

* cited by examiner

METHOD FOR DETERMINING A RELATIVE POSITION OF AN OBJECT IN RELATION TO AN X-RAY IMAGING APPARATUS

The present patent document claims the benefit of German Patent Application No. 10 2019 202 359.2, filed Feb. 21, 2019, which is hereby incorporated by reference.

TECHNICAL FIELD

The disclosure relates to a method for determining a relative position of an object in relation to an x-ray imaging apparatus, which has an x-ray source for creating an x-ray and an x-ray detector for creating a recorded image, wherein a distance from the object to the x-ray source and/or to the x-ray detector is established.

BACKGROUND

With x-ray images, the exact distance between the area of the body of a patient to be imaged by the x-ray image and the x-ray source or the x-ray detector may not be known a priori. This applies, in particular, to x-ray imaging apparatuses in which the x-ray source is arranged such that the x-ray source may be moved relative to the x-ray detector by a number of joints. In this case, the distance between the x-ray source and thus between the focus point and the x-ray detector cannot yet be established without an additional measuring instrument. But, even in x-ray imaging apparatuses with a constant distance between the focus point and the x-ray detector, such as in a C-arm device for example, the distance to the structure to be imaged in the body of the patient cannot readily be determined.

For some x-ray imaging apparatuses, at least the distance of the x-ray source and x-ray detector in relation to a patient couch on which the patient to be examined is lying during the imaging process is known. However, a precise determination of the distance to the body tissue to be imaged cannot be established solely from the knowledge of the relative position of the patient couch, because the distance between the body tissue to be imaged and the patient couch may vary under normal circumstances, depending on the type of body tissue and depending on the body structure of the patient, by up to 30 cm, in extreme cases by even more. Moreover, the distance from the patient couch is only known a priori for systems in which no movement of the x-ray imaging apparatus at right angles to the patient couch is possible. However, in many applications in hospitals, movable x-ray imaging apparatuses such as C-arm devices are employed precisely for real time support of examinations and surgical interventions.

A determination of the distance between a structure to be imaged by the x-ray imaging and the x-ray source that is as precise as possible and not just approximate is however desirable, especially because on the one hand a sufficiently high radiation dose is necessary for image quality that is as high as possible, especially for a high image resolution and a sufficient contrast, which scales quadratically at a distance from the x-ray source, but for medical reasons the patient is to be subjected to a radiation dose that is as low as possible. A precise knowledge of the position of the structure to be imaged thus allows the radiation dose to be reduced to the level still just required for the desired resolution, and thus allows the radiation load for the patient to be minimized.

SUMMARY AND DESCRIPTION

The scope of the present disclosure is defined solely by the appended claims and is not affected to any degree by the statements within this summary. The present embodiments may obviate one or more of the drawbacks or limitations in the related art.

The underlying object of the disclosure is to specify a method for an x-ray imaging apparatus by which, without any additional aids, a relative position of an object located in the ray path, such as a part of the body of a patient, may be determined as exactly as possible. The underlying object is further to specify an x-ray imaging apparatus that is configured for determination by such a method.

In one embodiment, a method for determining a relative position of an object in relation to an x-ray imaging apparatus is provided. The x-ray imaging apparatus includes at least one x-ray source with a variable focus point to create an x-ray and at least one x-ray detector to create a recorded image. The method includes bringing the object in the ray path of the x-ray into a first position, wherein the x-ray is generated by the x-ray source with and in particular at a first focus point, and by the x-ray focused at the first focus point a first image is recorded of the object in the first position. The method further includes imaging at least one defined geometry in and/or on the object to provide the first recorded image. At the x-ray source, a measure for varying the focus point towards a second focus point is taken, where the x-ray is generated by the x-ray source with and in particular at the second focus point, and by the x-ray focused on the second focus point a second recorded image of the object in the first position is created. The at least one defined geometry is imaged in the second recorded image. Additionally, a distance from the object to the x-ray source and/or to the x-ray detector is determined based on the change in the focus point as well as on the basis of the imagings of the at least one defined geometry in the first recorded image and the second recorded image.

The first or the second recorded image may be created by an x-ray absorption measurement. The object configured to be imaged may be one or more of a part of the body, a tissue structure in a part of the body of a patient, or a medical or other implant implanted in the body of a patient. In certain examples, the term implant may refer to implant aids such as screws etc. In certain examples, the object may be a bone that is to be imaged by the x-ray imaging, so that the distance from the bone to the x-ray source or to the x-ray detector is to be determined, wherein the bone is brought into a first position by the entire part of the body surrounding the bone being brought into an appropriate position.

A relative position of the object in relation to the x-ray imaging apparatus is to be understood here in particular as a reference system being defined in space by the x-ray source and the x-ray detector, so that the relative position of the object is defined by a distance to the x-ray source along the path from the focus of the x-ray source to the x-ray detector and, if necessary, also by a polar deflection with regard to the perpendicular from the x-ray source to the x-ray detector within a normal plane to the perpendicular. In particular, the distance from the x-ray source to the x-ray detector may be assumed at all times as given and known. The distance from the x-ray source, of which the focus may be assumed as punctiform, to the x-ray detector may be fixed.

In particular, the x-ray imaging apparatus may have more than one x-ray source and/or more than one x-ray detector. In this case, the method, if required, may be carried out separately for each individual possible pair of an x-ray source and an x-ray detector. A variable focus point of the x-ray source here in particular includes that the punctiform area by comparison with the orders of magnitude of the x-ray imaging apparatus at which an electron beam in an x-ray tube of the x-ray source strikes an anode material of the x-ray tube (known as a "focal spot"), may be changed along the anode material in such a way that the variation has a component at right angles to that direction of propagation of the x-ray that defines the decisive ray path for the recorded images.

In this sense, a measure for a change in the focus point through to a second focus point is to be understood in particular as a type of measure through which the focal spot is changed as described along the anode material, e.g., through an electromagnetic deflection of the electron beam in the x-ray tube. The measure then includes the case of the application of a corresponding voltage or of a corresponding current to an electromagnetic deflection apparatus, which may be provided by capacitor plates or deflection coils.

The object may be brought into the ray path of the x-ray leading from the x-ray source to the x-ray detector into the first position, by a patient, whose body tissue is to be imaged by the x-ray imaging, assuming a defined position on a patient couch for example, and subsequently by the patient couch being brought into a defined position in relation to the x-ray imaging apparatus. As an alternative to this, if the x-ray imaging apparatus is configured appropriately for this purpose, by the x-ray imaging apparatus—or at least parts of the apparatus, for example a subunit including the x-ray source—being moved in relation to fixed patient couch. The ray path here in particular includes the area of the propagation of the direction of propagation intended for the x-ray imagings, thus without an acute radiation having to be permanently present while the object in the ray path is brought into the first position.

The at least one defined geometry in and/or on the object is to be understood here as any structure that is suitable, according to its position relative to the object and according to its type, on the one hand for creating a sufficiently high contrast in order to be able to be identified in the recorded image, (e.g., also automatically), and on the other hand to have a sufficiently sharp edge for such an identification, in order to be able to be differentiated through this from the surrounding image areas. In this case, the position of the defined geometry in relation to the structure to be imaged in the object is such that information in respect of a distance from the geometry to the x-ray source and/or to the x-ray detector may also be transmitted without appreciable deviation to the structure to be imaged. A defined geometry in this case in particular includes bones or edges of bones of a part of a patient's body, or also a medical or other implant or at least an edge hereof as well as furthermore also an external marker to be attached separately to the object with an edge geometry which is easy to detect optically.

Initially, the first recorded image of the object is thus created, wherein the x-ray source is set such that the x-ray is focused on the first focus point. In the first recorded image, the at least one defined geometry, (e.g., a bone edge or an implant edge in the body tissue of a patient or an edge of an external marker attached to a part of the patient's body), is imaged and is subsequently detected automatically. Subsequently, the focus point of the x-ray source is changed, for example, as described by the application of a deflection voltage or a deflection current. Then, the x-ray is focused on the second focus point, so that the corresponding second recorded image created images the defined geometry in such a way that this appears slightly offset in relation to a fixed reference point such as a corner of the image area by comparison with the first recorded image. This offset may now be determined based on the defined geometry detected in the first recorded image and the second recorded image, in particular automatically (by an appropriate image recognition), wherein here too the determination in particular takes place automatically.

On the basis of the knowledge of the displacement of the second focus point in relation to the first focus point and also based on the knowledge of the distance between the x-ray source and the x-ray detector, the distance of the at least one defined geometry from the x-ray source and/or from the x-ray detector may now be established based on simple geometrical considerations by the set of rays, e.g., fully automatically, in particular without an intervention or any command by a user being required. On the basis of this distance, the distance of the object per se or of an actual area to be imaged located in the object to the x-ray source or to the x-ray detector may now be determined, be it by the distance of the defined geometry being used directly as a corresponding distance for a structure of interest to be imaged, or in accordance with predefined rules based on the distance of the defined geometry from the x-ray source and/or from the x-ray detector.

The fact that the change in focus point may be undertaken in the x-ray source itself means that neither a movement of the patient nor of the object nor any other additional aids, (e.g., an external measuring device to determine the distance sought), are required. In particular, it is advantageous here for many x-ray imaging apparatuses to be configured for this type of change of focus point in any event for reasons of calibration and the like, so that the method is able to be carried out on a plurality of x-ray imaging apparatuses without further changes in their structure, but a corresponding evaluation of the recorded images merely has to be carried out.

In an advantageous way, a determination of the distance sought using external aids, (e.g., optical measuring instruments), may thus be dispensed with, wherein moreover the imprecisions or inaccessibilities arising in optical measurements by the measurement area being covered, (e.g., by surgical drapes etc.), may be circumvented.

After the object has been brought into the first position, the remainder of the method acts, which only involve the x-ray source and/or the x-ray detector or the recorded images created by the device as well as the image recognition resulting therefrom and subsequent computations, may be carried out by an automatic routine.

Conveniently the same part of a collimator of the x-ray source will be imaged in each case in the first recorded image and in the second recorded image, wherein a value of the change in the focus point is established based on the respective imaging of the part of the collimator in the first recorded image and in the second recorded image, and wherein the value of the change is included for the establishment of the distance of the object to the x-ray source and/or to the x-ray detector. This means in particular that the x-ray emanating from the respective focus point is guided by the collimator such that at least the part of the collimator shades the created x-ray radiation from the x-ray detector. An edge and/or corner or another delimitation of the collimator may be imaged here in the first and the second recorded image as a part of the collimator. The distance of the collimator to the respective focus point is known for reasons of the required calibration of the x-ray imaging apparatus and also because of its construction. The part of the collimator, which is thus imaged in the two recorded images, may now serve as a reference, in order implicitly to establish the change in the focus point if this is difficult to define in absolute values. The use of a collimator as a reference of this type here has the advantage of no additional components or the like being required, because a collimator may be present in the x-ray imaging apparatus in any event for shielding the environment from a propagation of the x-rays outside the ray path intended for the recorded images.

A tissue structure of a patient and/or a structure implanted in a or in the patient may be imaged as at least one defined geometry in the object, wherein an implanted structure in particular includes a medical or other implant as well as corresponding implant aids (e.g., screws, etc.). Such an object has a suitably delimited edge for high-contrast imaging and thus for an automatic detection in the first and the second recorded image, and may moreover be chosen close to the relevant structure in the patient's body, which is to be imaged by the higher-ranking x-ray imaging, for which the method for determining the relative position is to be carried out.

Expediently, a marker is attached temporarily to a part of a patient's body, wherein the marker is imaged as at least one defined geometry on the object. This is in particular advantageous if the area to be imaged by the x-ray imaging does not have any sufficiently high-contrast bone structures, or if the area of the body to be imaged lies at only a slight depth below the skin in the direction of propagation of the x-ray. The temporary marker here has an easy-to-detect geometry, e.g., an L-shape or the like.

It further proves advantageous for a plurality of defined geometries at a different respective distance from the x-ray source and/or from the x-ray detector to be imaged in the first recorded image and in the second recorded image in each case, wherein for each of these geometries the distance to the x-ray source or to the x-ray detector is established in each case, and wherein the distance of the object to the x-ray source or to the x-ray detector is established on the basis of the distances of the geometries established. The distance of the object from the x-ray source or from the x-ray detector may be determined as a simple average or a weighted average of the established distances. The weighting may be undertaken, for example, based on anatomical knowledge via the respective distance of the individual geometries from one another and, if necessary, from the object to be imaged. On the one hand, this improves the precision of the determination, and on the other hand, in this way, it is also possible to establish a distance to an object in an area of the body, which has a no structure easily able to be detected which may serve as a defined geometry in the immediate vicinity.

In an advantageous embodiment, structures imaged in the first recorded image are related to a reference point. In the second recorded image, a change in the corresponding imaged structures occurring through the change in the focus point in relation to the reference point is corrected to the extent that the structures imaged in the second recorded image each have the same relationship to the reference point as the respective corresponding structures imaged in the first recorded image. Through this, a corrected second recorded image is created. In other words, through the shifting of the focus point in the first recorded image and in the second recorded image, the areas of the image in which the same tissue structure is imaged in each case are slightly offset from one another. This offsetting may now be corrected retrospectively, wherein in particular the knowledge of the shift of the first focus point towards the second focus point may be included. As a result, image areas that image the same tissue structure cover the same area in the first and the second recorded image except for negligible imaging errors.

Conveniently, a video sequence is created here based on the first recorded image and based on the corrected second recorded image. In particular, a plurality of first recorded images may be created, for which the x-ray is focused on the first focus point, and a further plurality of second recorded images, for which the x-ray is focused on the second focus point. The individual first recorded images and second recorded images directly alternate for the video sequence or groups of first recorded images alternate with groups of second recorded images. The groups of first or second recorded images here may each include a single-digit or low two-digit number of corresponding recorded images.

X-ray imaging apparatuses, (e.g., C-arm devices), may be used for support during operative interventions. Video sequences of x-ray images may be created here. The proposed embodiment allows the recorded images created for the method for determining the relative position to be used directly for the video sequences after appropriate image processing.

In another embodiment, an x-ray imaging apparatus is provided, wherein the apparatus includes at least one x-ray source with a variable focus point for creating an x-ray and at least one x-ray detector for creating a recorded image. The x-ray imaging apparatus is configured, based on at least two different images of defined geometries on or in an object positioned in the ray path of the x-ray, which are shown on at least two different recorded images of the x-ray imaging apparatus, to determine a distance of the object from the x-ray source and/or from the x-ray detector, if the at least two recorded images have each been recorded by x-rays with a different focus point. The x-ray imaging apparatus shares the advantages of the method described herein for determining a relative position of an object in relation to an x-ray imaging apparatus. The advantages stated for the method and for its developments may be transferred here by analogy to the x-ray imaging apparatus. In particular, the x-ray imaging apparatus in this case includes a control unit that may be configured for automatic determination of the distance of the object to the x-ray source and/or to the x-ray detector, as well as for change in the focus point.

In particular, the x-ray imaging apparatus may also have more than one of the x-ray sources embodied as stated and/or more than one x-ray detector. The x-ray imaging apparatus may be embodied as a mobile C-arm device. An x-ray source in a C-arm device, depending on application, may be at a variable distance from the object to be imaged, whereby the above-mentioned embodiment, which enables the x-ray imaging apparatus to determine the distance to the object, is especially advantageous.

The disclosure further gives a method for automatic positioning of an object in relation to an x-ray imaging apparatus having at least one x-ray source with a variable focus point for creating an x-ray and at least one x-ray detector for creating a recorded image. In the method, a required distance of the object from the x-ray source and/or from the x-ray detector is predetermined. The object in the ray path of the x-ray is brought into a first position. An actual distance of the object to the x-ray source and/or to the x-ray detector is determined by the method described above for determining the relative position. Furthermore, the relative position of the object in relation to the x-ray imaging apparatus is changed as a function of the predetermined required distance and the actual distance determined. The required distance may be predetermined here in particular automatically as a function of the requirements for the resolution during the imaging and/or medical considerations.

The method for automatic positioning shares the advantages of the method for determining a relative position of an object in relation to an x-ray imaging apparatus. The advantages stated for the method for determining a relative position and for its developments may be transferred here by analogy to the method for automatic positioning. A radiation dose of the x-ray source may be set here as a function of the actual distance of the object to the x-ray source established.

BRIEF DESCRIPTION OF THE DRAWINGS

An exemplary embodiment of the disclosure is explained below based on the figures. In the figures, in schematic diagrams in each case.

Parts and variables corresponding to one another are provided with the same reference characters in all figures in each case.

DETAILED DESCRIPTION

Figure 1:
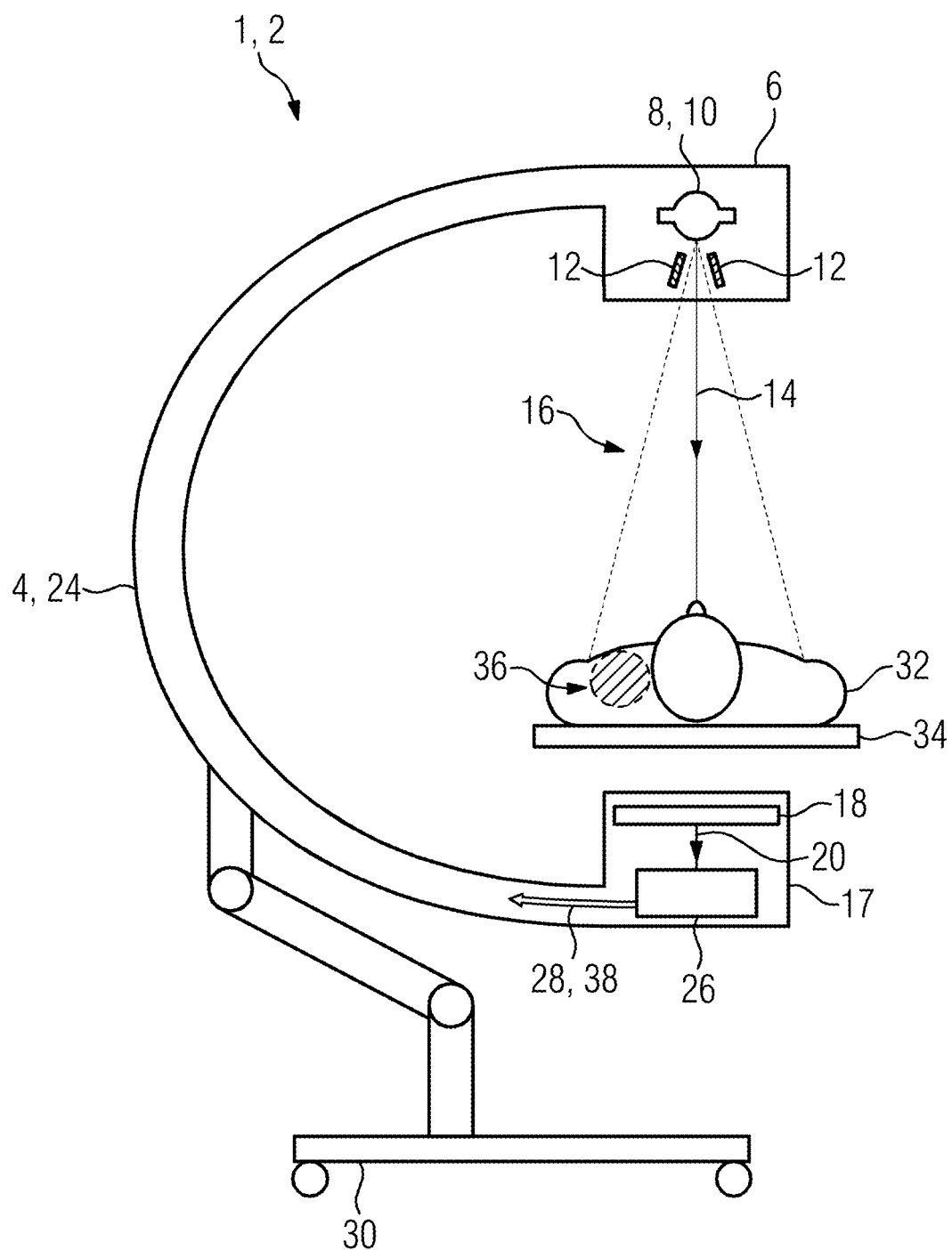
FIG. 1 depicts an example of a C-arm device in a cross-sectional diagram.

FIG. 1 depicts a schematic in a cross-sectional diagram of an x-ray imaging device 1, which in the present example is embodied as a C-arm device 2. The C-arm device 2 has a C-arm 4, on which at the end 6 shown at the top in the diagram an x-ray tube 8 is arranged as an x-ray source 10. Furthermore collimators 12 are arranged in the immediate vicinity of the x-ray tube 8 at the upper end 6 of the C-arm 4, which align an x-ray 14 generated by the x-ray tube 8 on a ray path 16. An x-ray detector 20 is arranged on the end 18 of the C-arm 4 shown at the bottom in FIG. 1. Not shown here in FIG. 1 are additional components for signal processing and bundling of the image data 20 created by the x-ray detector 18.

The C-arm 4 furthermore has a control unit 26 within its housing 24, which is configured to create finished recorded images 28 from the image data 20 and also control all the relevant processes for the creation of the recorded images 28 in the x-ray imaging apparatus 1, thus for example the start time and the value of the anode voltage of the x-ray tube 8, or also the respective operating voltages of detector modules in the x-ray detector 18. The control unit 26 is shown here for the sake of simplicity as an integrated unit but may also be realized however by different decentralized units, which take over the required functions. The control unit 26 here has the required number of processors, physical memory chips, microcontrollers, baseboards, and the like.

The housing 24 of the C-arm 4 is mounted on a chassis 30, so that the C-arm device 2 as such for creating the recorded images 28 may be moved to different deployment locations, and moreover is able to be moved in relation to a patient 32 of whom a region of their body is to be imaged by x-ray imagings. The patient 32 lies on a patient couch 34 here. In order now to image an object 36, (e.g., a part of the body of the patient 32 or also a bone structure by the C-arm device 2), the C-arm 4 on the chassis 30 will be brought into a suitable position in relation to the patient 32 for this purpose. The recorded images 28 created there may then be output via a data connection 38 to a computer not shown in any greater detail for graphical display etc.

During the creation of the recorded images 28, however, the distance DSO from the object 36 to the x-ray source 10 is unknown, as is the distance DOI from the object to the x-ray detector 18. Only the fixed predetermined distance DSI from the x-ray source 10 to the x-ray detector 18 is known here. In a way still to be illustrated, the distance DSO and also the distance DIO may now be determined based on the various recorded images, which are each created with a different focus point in the x-ray tube 8.

Figure 2:
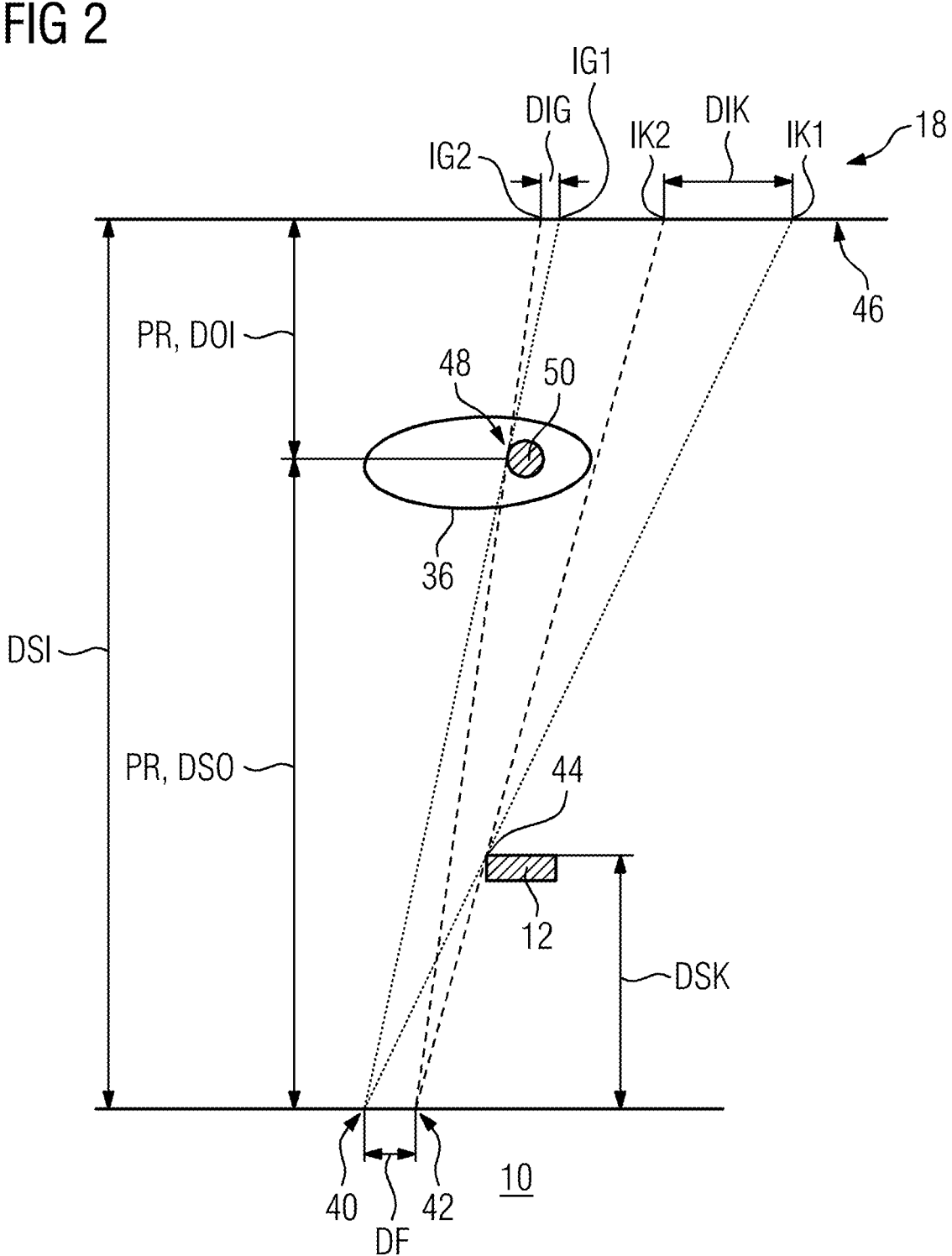
FIG. 2 depicts an example of a determination of the distance from an object in the C-arm device according to FIG. 1 by various focus points in the x-ray source in a geometrical diagram.

FIG. 2 depicts schematically in a geometrical illustrative diagram the ray path 16 for the x-ray 14 according to FIG. 1, wherein to create the ray 14 in FIG. 2 a first focus point 40 is used once and a second focus point 42 is used once. The diagram in FIG. 2 is not to be seen here as true-to-scale. The distance DSO from the x-ray source 10 to the object 36 or also the distance DOI from the object to the image plane 46 and thus to the detector 18 may be established here as the relative position PR of the object 36 (which is given by a part of the body or a body tissue structure of the patient 32 according to FIG. 1). For the x-ray focused on the first focus point 40, an edge 44 of the collimator 12 in the image plane 46, which is given by the x-ray detector 18, is imaged at IK1 (dotted-line ray). A defined geometry 48 in the object 36, which is given in the present case by a delimitation of a bone 50, is imaged by the x-ray focused at the first focus point 40 on a point IG1 in the image plane 46 (dotted-line ray). The corresponding image points in the image plane 46 for the edge 44 of the collimator 12 and for the geometry 48 are given by the x-ray focused on the second focus point 42 by IK2 or IG2 (dashed ray in each case).

Because the vertical distance DSK from the first focus point 40 or second focus point 42 to the edge 44 of the collimator 12 for both focus points 40, 42 may be assumed in the present example as the same (if this assumption is not made, the respective vertical distances of the focus points 40, 42 to the edge 44 are still known, the equations below are to be adapted here in a simple manner), and is known, the distance DF between the first focus point 40 and the second focus point 42 may be established from the distance DSI between the x-ray source 10 and the x-ray detector 18, the distance DSK from a focus point to the edge 44 of the collimator 12 as well as from the distance DIK of the two image points IK1 and IK2 in the image plane 46 via a simple set of rays. The result is provided in equation (i) below:

$$DF = DSK \cdot DIK/(DSI-DSK) \quad (i)$$

On the basis of the distance DF of the two focus points 40, 42 established in this way, using similar considerations, the distance DSO from the x-ray source 10 to the object 36 may be established from the distance DIG of the two image points IG1 and IG2 of the defined geometry 48 as provided in equation (ii) below:

$$DSO = DF \cdot (DSI-DSO)/DIG => DSO = DF \cdot DSI/(DF+DIG), \quad (ii)$$

with DF according to equation (i). A determination of the distance DIO from the object 36 to the x-ray detector 18 may be carried out in a similar way. Instead of the edge of the bone 50, or in addition thereto, a separately provided marker, not shown in any greater detail in FIG. 2, may be attached to the object 36 as the defined geometry.

Figure 3:
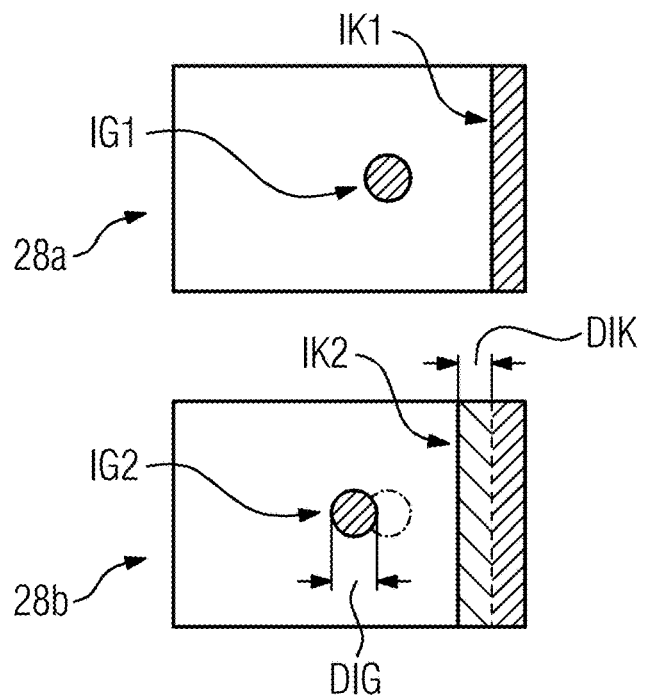
FIG. 3 depicts an example of two recorded images of the C-arm device according to FIG. 1 created by different focus points.

FIG. 3 depicts a schematic of a view of a first recorded image 28a and a second recorded image 28b in the setup shown in FIG. 2, wherein the first recorded image 28a has been created with an x-ray 14 focused on the first focus point 40, and the second recorded image 28b with an x-ray focused on the second focus point 42. Clearly to be seen in the second recorded image 28b is the relative shift of the image points IG2 and IK2 of the defined geometry 48 or of the edge 44 of the collimator 12 in relation to the corresponding image points IG1, IK2, as well as the distances DIG, DIK resulting herefrom, based on which by the geometrical considerations shown in FIG. 2, the distance DSO from the x-ray source 10 to the object 36 or the distance DOI from the object 36 to the x-ray detector 18 is determined.

Figure 4:
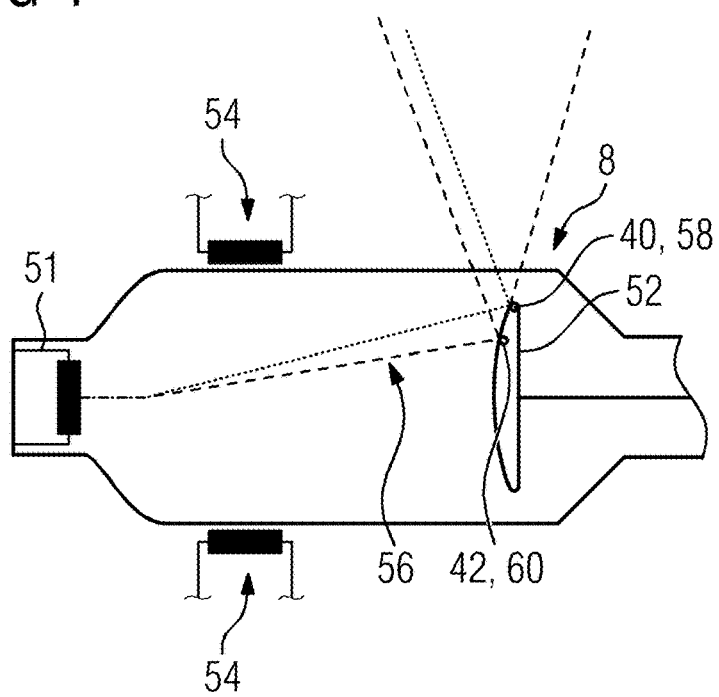
FIG. 4 depicts an example of an x-ray tube in a longitudinal cross-section.

FIG. 4 depicts a schematic diagram of a longitudinal section of an x-ray tube 8, which as well as a cathode 51 has a rotating anode 52 as well as deflection coils 54. By the deflection coils 54, the focal spot is able to be changed on the rotating anode 52, by different strengths of deflection current being applied to the deflection coils and thus creating different strengths of magnetic field to deflect the electron beam 56. The electron beam 56 in this case may be directed to a first focal spot 58 on the rotating anode 52, so that the x-ray 14 resulting herefrom is focused on the first focus point 40, which coincides with the first focal spot 58 (dotted lines). With a change in the deflection current in the deflection coils 54, the electron beam 56 may be directed to a second focal spot 60, so that the x-ray 14 resulting herefrom is focused on the second focus point 42, which coincides with the second focal spot 60 (dashed lines).

Figure 5:
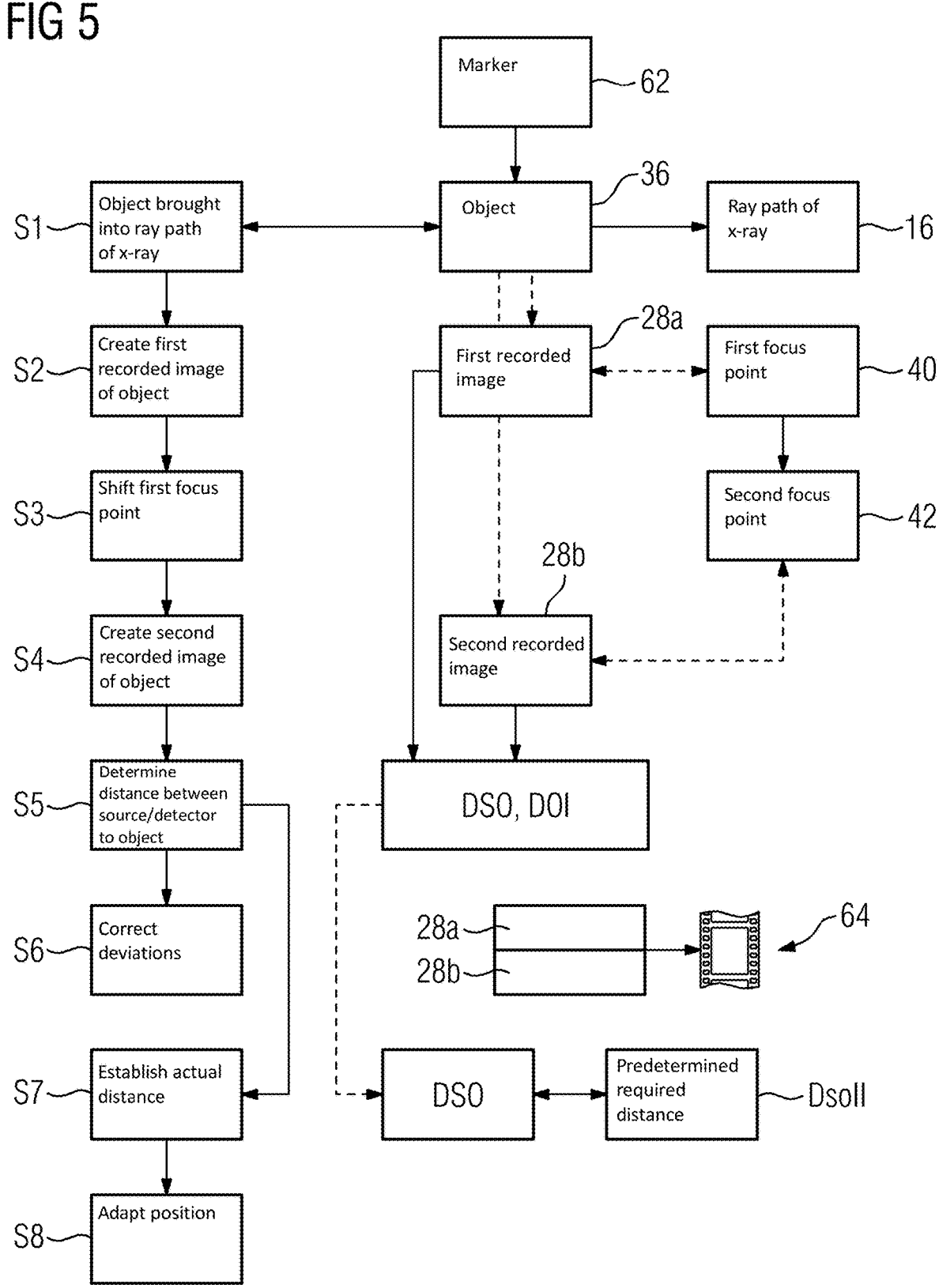
FIG. 5 depicts an example of a method for determining a relative position of an object in relation to the C-arm device according to FIG. 1 in a block diagram.

FIG. 5 depicts schematically in a block diagram a method for determining a relative position of an object 36 in relation to an x-ray imaging apparatus 1 according to FIG. 1. In an act S1, the object 36 is brought into the ray path 16 of the x-ray 14. In the present example, a marker 62 is also attached to the object. In an act S2, a first recorded image 28a of the object 36 is created, in which inter alia the marker 62 is able to be resolved as a defined geometry 48. For the first recorded image 28a, the x-ray 14 is focused on the first focus point 40. Now, in an act S3, the first focus point 40 is shifted towards the second focus point 42, e.g., using a change in the deflection current in the deflection coils 54 according to FIG. 4. In an act S4, a second recorded image 28b of the object 36 is created by the x-ray 14 focused on the second focus point 42. Now, in an act S5, based on the different imagings in the first recorded image 28a and the second recorded image 28b of the defined geometry 48 in accordance with geometrical considerations shown in FIG. 2, the distance DSO from the x-ray source 10 to the object 36 as well the distance DOI from the object 36 to the x-ray detector 18 is determined.

In an additional act S6, the deviations visible in FIG. 4 in the imaging of corresponding structures, which are produced in relation to one another in the first recorded image 28a and the second recorded image 28b, may be corrected such that corresponding structures are imaged in the same image areas. The corrections may allow for a video sequence 64 to be created based on the first and the second recorded image 28a, 28b, on the basis of which, for example, an accompanying surgical intervention may be monitored.

The method of acts S1 to S5 may moreover be embedded in a method for automatic positioning of an object in relation to an x-ray imaging apparatus. For this, in an act S7, the distance DSO established as actual distance may be compared with a predetermined required distance Dsoll, and if there is too great a deviation, the position of the C-arm device 2 may be adapted according to FIG. 1 in an act S8.

Moreover, in an adaptation of this type, the radiation strength of the x-ray source 8 may be configured to a new actual distance.

Although the disclosure has been illustrated and described in greater detail by the exemplary embodiments, the disclosure is not restricted by these exemplary embodiments. Other variations may be derived herefrom by the person skilled in the art, without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for determining a relative position of an object in relation to an x-ray imaging apparatus having an x-ray source with a variable focus point for creating x-rays and an x-ray detector for creating recorded images, the method comprising:

positioning the object in a ray path of a first x-ray in a first position of the object in relation to the x-ray source and the x-ray detector of the x-ray imaging apparatus, wherein the object is positioned between the x-ray source and the x-ray detector in the first position, and wherein the first x-ray is created with a first focus point by the x-ray source and by the first x-ray focused on the first focus point;

creating a first recorded image of the object in the first position with the first focus point, wherein at least one defined geometry in the object and/or on the object is imaged in the first recorded image;

undertaking a measure for a change in focus point towards a second focus point at the x-ray source with the x-ray source, the x-ray detector, and the object remaining in the first position, wherein a second x-ray with the second focus point is created by the x-ray source and by the second x-ray focused on the second focus point;

creating a second recorded image of the object in the first position with the second focus point, wherein the at least one defined geometry is imaged in the second recorded image, and wherein a same part of a collimator of the x-ray source is imaged in both the first recorded image and the second recorded image; and determining a distance from the object to the x-ray source and/or to the x-ray detector based on the change in the focus point between the first focus point and the second focus point and the recorded images of the at least one defined geometry in the first recorded image and the second recorded image, wherein a value of the change in the focus point is established based on the respective imaging of the same part of the collimator in the first recorded image and the second recorded image, and wherein the value of the change in the focus point is included for the determination of the distance of the object to the x-ray source and/or to the x-ray detector.

2. The method of claim 1, wherein a plurality of defined geometries each at a different distance from the x-ray source and/or from the x-ray detector is imaged in the first recorded image and the second recorded image,
  wherein the respective distance to the x-ray source or to the x-ray detector is established for each defined geometry of the plurality of defined geometries, and
  wherein the distance of the object to the x-ray source or to the x-ray detector is established based on the established distances of the plurality of defined geometries.

3. The method of claim 1, wherein structures imaged in the first recorded image are related to a reference point,
  wherein, in the second recorded image, a change in the corresponding imaged structures in relation to the reference point occurring through the change in the focus point is corrected such that the structures imaged in the second recorded image each have a same relationship to the reference point as the respective structures imaged in the first recorded image, and
  wherein a corrected second recorded image is created based on this same relationship to the reference point.

4. The method of claim 3, wherein a video sequence is created based on the first recorded image and the corrected second recorded image.

5. The method of claim 1, wherein the at least one defined geometry in the object comprises a tissue structure of a patient, a structure implanted into the patient, or a combination thereof.

6. The method of claim 1, wherein a marker is attached to a part of a body of a patient, and wherein the marker is imaged as the at least one defined geometry on the object.

7. The method of claim 1, wherein the object is a part of a body of a patient.

8. The method of claim 7, wherein the part of the body of the patient is a bone structure of the body of the patient.

9. A method for determining a relative position of an object in relation to an x-ray imaging apparatus having an x-ray source with a variable focus point for creating x-rays and an x-ray detector for creating recorded images, the method comprising:
  positioning the object in a ray path of a first x-ray in a first position of the object in relation to the x-ray source and the x-ray detector of the x-ray imaging apparatus, wherein the object is positioned between the x-ray source and the x-ray detector in the first position, and wherein the first x-ray is created with a first focus point by the x-ray source and by the first x-ray focused on the first focus point;
  creating a first recorded image of the object in the first position with the first focus point;
  undertaking a measure for a change in focus point towards a second focus point at the x-ray source with the x-ray source, the x-ray detector, and the object remaining in the first position, wherein a second x-ray with the second focus point is created by the x-ray source and by the second x-ray focused on the second focus point;
  creating a second recorded image of the object in the first position with the second focus point, wherein a plurality of defined geometries each at a different distance from the x-ray source and/or from the x-ray detector is imaged in the first recorded image and the second recorded image; and
  determining a distance from the object to the x-ray source and/or to the x-ray detector based on the change in the focus point between the first focus point and the second focus point and the first and second recorded images,
  wherein a respective distance to the x-ray source or to the x-ray detector is established for each defined geometry of the plurality of defined geometries in the first recorded image and the second recorded image, and
  wherein the distance of the object to the x-ray source or to the x-ray detector is established based on the established distances of the plurality of defined geometries.

10. The method of claim 9, wherein structures imaged in the first recorded image are related to a reference point,
  wherein, in the second recorded image, a change in the corresponding imaged structures in relation to the reference point occurring through the change in the focus point is corrected such that the structures imaged in the second recorded image each have a same relationship to the reference point as the respective structures imaged in the first recorded image, and
  wherein a corrected second recorded image is created based on this same relationship to the reference point.

11. The method of claim 10, wherein a video sequence is created based on the first recorded image and the corrected second recorded image.

12. The method of claim 9, wherein the object is a part of a body of a patient.

13. The method of claim 9, wherein at least one defined geometry of the plurality of defined geometries in the object comprises a tissue structure of a patient, a structure implanted into the patient, or a combination thereof.

14. The method of claim 9, wherein a marker is attached to a part of a body of a patient, and
  wherein the marker is imaged as at least one defined geometry of the plurality of defined geometries.

15. A method for automatic positioning of an object in relation to an x-ray imaging apparatus having an x-ray source with a variable focus point to create x-rays and an x-ray detector to create recorded images, the method comprising:
  predetermining a required distance of the object to the x-ray source and/or to the x-ray detector;
  positioning the object in a ray path of a first x-ray in a first position of the object in relation to the x-ray source and the x-ray detector of the x-ray imaging apparatus, wherein the object is positioned between the x-ray source and the x-ray detector in the first position, and wherein the first x-ray is created with a first focus point by the x-ray source and by the first x-ray focused on the first focus point;
  creating a first recorded image of the object in the first position, wherein at least one defined geometry in the object and/or on the object is imaged in the first recorded image;
  undertaking a measure for a change in focus point towards a second focus point at the x-ray source with the x-ray source, the x-ray detector, and the object remaining in the first position, wherein a second x-ray with the second focus point is created by the x-ray source and by the second x-ray focused on the second focus point;
  creating a second recorded image of the object in the first position, wherein the at least one defined geometry is imaged in the second recorded image, wherein a same part of a collimator of the x-ray source is imaged in both the first recorded image and the second recorded image; and
  determining an actual distance of the object to the x-ray source and/or to the x-ray detector based on the change in the focus point between the first focus point and the second focus point and the recorded images of the at least one defined geometry in the first recorded image and the second recorded image, wherein a value of the change in the focus point is established based on the respective imaging of the same part of the collimator in the first recorded image and the second recorded image, and wherein the value of the change in the focus point is included for the determination of the actual distance of the object to the x-ray source and/or to the x-ray detector; and changing a relative position of the object in relation to the x-ray source and the x-ray detector of the x-ray imaging apparatus as a function of the predetermined required distance and the actual distance determined.

16. The method of claim 15, further comprising:
setting a radiation dose based on a new actual distance of the object to the x-ray source and/or the x-ray detector following the changing of the relative position of the object.

17. The method of claim 15, wherein the at least one defined geometry in the object comprises a tissue structure of a patient, a structure implanted into the patient, or a combination thereof.

18. The method of claim 15, wherein a marker is attached to a part of a body of a patient, and
wherein the marker is imaged as the at least one defined geometry on the object.

19. An x-ray imaging apparatus comprising:
an x-ray source having a variable focus point configured to create x-rays; and
an x-ray detector configured to create recorded images, wherein the x-ray imaging apparatus is configured to:
record a first image of an object in a first position of the object in relation to the x-ray source and the x-ray detector with a first focus point of the x-ray source, wherein the object is positioned between the x-ray source and the x-ray detector in the first position, and wherein at least one defined geometry in the object and/or on the object is imaged in the first image;

change a focus point towards a second focus point at the x-ray source with the x-ray source, the x-ray detector, and the object remaining in the first position;

record a second image of the object in the first position with the second focus point of the x-ray source, wherein the at least one defined geometry in the object and/or on the object is imaged in the second image, wherein a same part of a collimator of the x-ray source is imaged in both the first image and the second image; and determine a distance from the object to the x-ray source and/or to the x-ray detector based on the change in the focus point between the first focus point and the second focus point and the recorded images of the at least one defined geometry in the first image and the second image, wherein a value of the change in the focus point is established based on the respective imaging of the same part of the collimator in the first image and the second image, and wherein the value of the change in the focus point is included for the determination of the distance from the object to the x-ray source and/or to the x-ray detector.

20. The x-ray imaging apparatus of claim 19, wherein the x-ray imaging apparatus is a C-arm device.

* * * * *